United States Patent
Heidemann et al.

(10) Patent No.: US 10,780,428 B2
(45) Date of Patent: Sep. 22, 2020

(54) METHOD FOR PRODUCING MECHANICALLY STABLE CATALYSTS FOR HYDROGENATING CARBONYL COMPOUNDS, SAID CATALYSTS AND HYDROGENATING METHOD

(71) Applicant: BASF SE, Ludwigshafen (DE)

(72) Inventors: Thomas Heidemann, Ludwigshafen (DE); Barbara Wucher, Ludwigshafen (DE); Thomas Koelker, Düsseldorf-Holthausen (DE); Michel Pepers, Düsseldorf-Holthausen (DE); Ulf Brinkmann, Düsseldorf-Holthausen (DE); Magnus Topphoff, Düsseldorf-Holthausen (DE); Horst Josten, Düsseldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/347,619

(22) PCT Filed: Nov. 9, 2017

(86) PCT No.: PCT/EP2017/078703
§ 371 (c)(1),
(2) Date: May 6, 2019

(87) PCT Pub. No.: WO2018/091342
PCT Pub. Date: May 24, 2018

(65) Prior Publication Data
US 2019/0262808 A1  Aug. 29, 2019

(30) Foreign Application Priority Data

Nov. 15, 2016 (EP) ..................... 16198921

(51) Int. Cl.
| | | |
|---|---|---|
| *C07C 29/00* | (2006.01) | |
| *B01J 27/00* | (2006.01) | |
| *B01J 23/00* | (2006.01) | |
| *B01J 27/232* | (2006.01) | |
| *B01J 35/00* | (2006.01) | |
| *B01J 35/02* | (2006.01) | |
| *B01J 37/00* | (2006.01) | |
| *B01J 37/14* | (2006.01) | |
| *B01J 37/18* | (2006.01) | |
| *C07C 29/154* | (2006.01) | |
| *B01J 23/80* | (2006.01) | |
| *B01J 37/03* | (2006.01) | |

(52) U.S. Cl.
CPC ........... *B01J 27/232* (2013.01); *B01J 23/007* (2013.01); *B01J 23/80* (2013.01); *B01J 35/002* (2013.01); *B01J 35/0026* (2013.01); *B01J 35/026* (2013.01); *B01J 37/0063* (2013.01); *B01J 37/14* (2013.01); *B01J 37/18* (2013.01); *C07C 29/154* (2013.01); *B01J 37/031* (2013.01)

(58) Field of Classification Search
CPC ........ B01J 27/232; B01J 23/007; B01J 23/80; C07C 29/154
See application file for complete search history.

(56) References Cited

U.S. PATENT DOCUMENTS

| | | | |
|---|---|---|---|
| 7,084,312 B1 | 8/2006 | Huber et al. | |
| 7,442,810 B2 * | 10/2008 | Roesch | C07D 307/08 |
| | | | 549/295 |
| 2003/0187309 A1 | 10/2003 | Prinz et al. | |
| 2007/0135650 A1 | 6/2007 | Rosch et al. | |
| 2015/0314273 A1 | 11/2015 | Paulus et al. | |
| 2017/0113209 A1 | 4/2017 | Paulus et al. | |

FOREIGN PATENT DOCUMENTS

| | | |
|---|---|---|
| DE | 10357715 A1 | 7/2005 |
| DE | 102012019123 A1 | 4/2014 |
| DE | 102014004413 A1 | 10/2015 |
| EP | 2096098 A1 | 9/2009 |
| WO | WO-01/17934 A1 | 3/2001 |

OTHER PUBLICATIONS

International Search Report for PCT Patent Application No. PCT/EP2017/078703, dated Feb. 19, 2018.

* cited by examiner

*Primary Examiner* — Sikarl A Witherspoon
(74) *Attorney, Agent, or Firm* — Marshall, Gerstein & Borun LLP

(57) ABSTRACT

A process for producing a metal carbonate-containing shaped catalyst body for the hydrogenation of an organic compound having one or more carbonyl group, in which a) a metal carbonate composition which contains, based on the total weight of the metal carbonate composition, from 70 to 94.5% by weight of a metal carbonate mixture containing two or more than two metal carbonates of two or more than two different metals (M), from 5 to 25% by weight of metallic copper, and from 0.5 to 5% by weight of tableting aid is provided, b) a shaped body is formed from the metal carbonate composition provided in step a), and c) the shaped body obtained in step b) is activated in the presence of hydrogen at a temperature in the range from 150 to 250° C.

20 Claims, No Drawings

METHOD FOR PRODUCING MECHANICALLY STABLE CATALYSTS FOR HYDROGENATING CARBONYL COMPOUNDS, SAID CATALYSTS AND HYDROGENATING METHOD

CROSS-REFERENCE TO RELATED APPLICATIONS

This application is the U.S. National Stage application of International Patent Application No. PCT/EP2017/078703, filed Nov. 9, 2017, which claims the benefit of European Patent Application No. 16198921.5, filed Nov. 15, 2016.

FIELD OF THE INVENTION

The present invention relates to a process for producing a metal carbonate-comprising shaped catalyst body for the hydrogenation of an organic compound having one or more carbonyl group(s). The invention further relates to metal carbonate-comprising shaped catalyst bodies obtainable by means of the process according to the invention.

PRIOR ART

The catalytic hydrogenation of carbonyl compounds such as aldehydes, ketones, carboxylic acids and carboxylic esters plays an important role in the chemical industry, especially in the processes for producing basic chemicals. In catalytic hydrogenation, a variety of homogeneous and heterogeneous hydrogenation catalysts are used. Heterogeneous hydrogenation catalysts which are usually employed in various three-dimensional forms, e.g. as powder, granules or defined shaped bodies, in fluidized-bed or fixed-bed processes are of particular importance in industry. The most widespread processes here are fixed-bed processes in which defined shaped catalyst bodies are generally used.

In fixed-bed processes, the shaped catalyst bodies are usually subjected to high mechanical stresses. A low mechanical stability of the shaped catalyst bodies generally leads to premature disintegration of the catalyst and thus to a reduced period of use or frequent downtimes of the hydrogenation reactors equipped with the shaped catalyst bodies. To prevent excessive disintegration of the catalyst, the mechanical stress has to be kept as low as possible, which generally leads to a lower reactor loading. Apart from the catalytic activity, the mechanical stability of the shaped catalyst bodies used therefore also has a considerable influence on the economics of catalytic hydrogenation processes.

To increase the catalytic activity and/or the mechanical stability of shaped catalyst bodies, various approaches are followed in the prior art.

DE 102014004413 A1 describes, for example, the production of tableted shaped catalyst bodies for the hydrogenation of carbonyl compounds starting out from metal carbonate-comprising mixtures which have a higher metal surface area and thus a higher activity compared to the hydrogenation catalysts known in the prior art. In particular, a process for producing shaped Cu—Zn catalyst bodies, in which a mixture of Cu carbonate and zinc carbonate obtainable by means of precipitation is subjected to heat treatment at a temperature in the range from 150° C. to 350° C., giving a Cu—Zn carbonate mixture which has a molar ratio of Cu:Zn of about 1:2 and has a carbonate content of from 2.7 to 14.0% by weight and is subsequently tableted, is described.

EP 2096098 A1 describes a process for producing tableted shaped catalyst bodies having both a high mechanical stability and also a high hydrogenation activity, in which compounds of copper and zinc, especially copper carbonate and zinc carbonate, are coprecipitated on a support material composed of aluminum oxide powder, the resulting catalyst material is calcined, mixed with 5% by weight of graphite, tableted and the finished catalyst pellets are after-calcined.

DE 102012019123 A1 describes a process for producing tableted shaped Cu—Al catalyst bodies having a high lateral compressive strength and a high hydrogenation activity, in which a dry carbonate-comprising mixture comprising Cu, Al and Mn is firstly provided, and part of this carbonate-comprising mixture is calcined. The uncalcined, dry carbonate-comprising mixture is, after addition of graphite, either tableted directly or mixed with a proportion of the calcined carbonate-comprising mixture and then tableted after addition of graphite. The shaped Cu—Al catalyst bodies obtained in this way are optionally after-calcined.

Very hard and thus mechanically stable shaped catalyst bodies can be obtained by means of the calcination. However, heat treatments generally always lead to a more or less strong degree of sintering by means of which the size of the active catalyst surface and thus the hydrogenation activity of the catalysts is reduced. In order to obtain hydrogenation catalysts having a very high activity, the sintering effects caused by the heat treatment generally have to be kept very small.

DE 10357715 A1 describes a process for producing a hydrogenation catalyst, in which a mixture of copper carbonate and zinc carbonate is precipitated in the presence of a support consisting of aluminum oxide and zinc oxide. The suspension is subsequently filtered and the solid is dried and calcined. The calcined catalyst powder is mixed with 1.5% by weight of graphite and 5% by weight of copper powder, tableted and after-calcined. The shaped catalyst bodies obtained in this way have a composition of 66% of CuO, 24% of ZnO, 5% of $Al_2O_3$ and 5% of Cu.

WO 01/17934 A1 describes a process for producing tableted shaped catalyst bodies having both a high mechanical stability and also a high hydrogenation activity, in which pulverulent metallic copper and/or pulverulent cement is added to a mixture of various metal oxides and the mixture obtained in this way is subsequently shaped to give a shaped body.

The mechanical stability of the shaped catalyst bodies can be increased by addition of binders such as metal powders, for example metallic copper powder, and/or cement to the catalyst material. However, this leads to a reduction in the catalytic activity of the shaped catalyst bodies produced therefrom, since the proportion of active catalyst material is reduced by the addition of the binder.

DESCRIPTION OF THE INVENTION

It is an object of the present invention to provide a process for producing shaped catalyst bodies for the hydrogenation of carbonyl compounds starting out from metal carbonate-comprising mixtures, which shaped catalyst bodies are firstly mechanically stable, i.e. have a high lateral compressive strength, and secondly have an at least equivalent hydrogenation activity compared to shaped catalyst bodies which are based on the same catalyst material but have a lower strength.

It has now surprisingly been found that the addition of metallic copper to a metal carbonate mixture comprising two or more than two metal carbonates of two or more than two different metals leads, after tableting and activation, to shaped catalyst bodies which not only have a significantly increased stability but also an increased hydrogenation activity compared to shaped catalyst bodies which have been produced from the same metal carbonate mixture but without the addition of metallic copper.

Accordingly, the present invention firstly provides a process for producing a shaped catalyst body, wherein a) a metal carbonate-comprising composition which comprises, based on the total weight of the metal carbonate-comprising composition,
   from 70 to 94.5% by weight of a metal carbonate mixture comprising two or more than two metal carbonates of two or more than two different metals (M),
   from 5 to 25% by weight of metallic copper and
   from 0.5 to 5% by weight of tableting aid
   is provided,
b) a shaped body is formed from the metal carbonate-comprising composition provided in step a) and
c) the shaped body obtained in step b) is activated in the presence of hydrogen at a temperature in the range from 150 to 250° C.

Furthermore, it has been found that the hydrogenation activity of the shaped catalyst bodies can be increased further when the shaped catalyst body obtained after tableting is subjected to a thermal treatment in the absence of hydrogen at a temperature in the range from 150 to 350° C. before activation in the presence of hydrogen.

The present invention therefore secondly provides a process for producing a shaped catalyst body as defined above, wherein the shaped body obtained in step b) is firstly subjected to a first thermal treatment at a temperature in the range from 150 to 350° C. in the absence of hydrogen in a step c1) and the shaped body which has been thermally treated in this way is subsequently activated at a temperature in the range from 150 to 250° C. in the presence of hydrogen in a step c2).

The present invention further provides shaped catalyst bodies obtainable by one of the above-defined processes.

The present invention further provides a process for the hydrogenation of an organic compound having one or more than one carbonyl group(s), wherein the organic compound is brought into contact in the presence of hydrogen with a shaped catalyst body obtainable by means of one of the processes defined above and below.

Step a) of the Process

In step a) of the process of the invention for producing a shaped catalyst body, a metal carbonate-comprising composition which comprises, based on the total weight of the metal carbonate-comprising composition,
   from 70 to 94.5% by weight of a metal carbonate mixture comprising two or more than two metal carbonates of two or more than two different metals (M),
   from 5 to 25% by weight of metallic copper and
   from 0.5 to 5% by weight of tableting aid
   is provided.

The metal carbonate-comprising composition provided in step a) comprises, as main component, from 70 to 94.5% by weight, preferably from 76 to 92.5% by weight, in particular from 82 to 89% by weight, of a metal carbonate mixture.

According to the invention, the metal carbonate mixture used in step a) comprises two or more than two metal carbonates of two or more than two different metals (M).

The metal carbonate mixture used in step a) preferably comprises from 2 to 10 metal carbonates of from 2 to 10 different metals (M).

The metal carbonate mixture used in step a) particularly preferably comprises from 2 to 5 metal carbonates of from 2 to 5 different metals (M).

In particular, the metal carbonate mixture used in step a) comprises from 2 to 5 metal carbonates of 2 or 3 different metals (M).

The metal carbonates which are used for producing the metal carbonate-comprising composition can be present as "pure" metal carbonates of the general formula $$M_{2n/m}^{m+}(CO_3^{2-})n,$$

where n and m are each an integer from 1 to 4, and/or in the form of metal hydroxycarbonates, known as basic metal carbonates, of the general formula $$x[M_{2r\nu m}^{m+}(CO_3^{2-})_n]\cdot y[M_{l/m}^{m+}(OH^-)_l],$$

where l, m, n, x and y are each an integer from 1 to 4. In addition, both the "pure" metal carbonates and also the metal hydroxy carbonates can comprise various amounts of water of crystallization.

Accordingly, the expression "metal carbonates" as used for the purposes of the present invention encompasses metal carbonates and/or metal hydroxycarbonates and also the hydrates thereof.

The metal carbonates which are used for producing the metal carbonate-comprising composition can be present as "pure" metal carbonates of the general formula $$M^{2+}(CO_3^{2-})$$

and/or as metal hydroxycarbonates of the general formula $$x[M^{2+}(CO_3^{2-})]\cdot y[M^{2+}(OH^-)_2],$$

where x and y are each an integer from 1 to 3. In addition, both the "pure" metal carbonates and also the metal hydroxycarbonates can comprise various amounts of water of crystallization.

As metal (M), it is generally possible to use all metals known to those skilled in the art which are suitable for the hydrogenation of carbonyl compounds. The metal (M) is preferably selected from among transition metals of groups 8, 9, 10, 11 and 12 of the IUPAC Periodic Table. The metal (M) is particularly preferably selected from among Co, Ni, Cu, Au, Zn, Cd, Ru and Fe, in particular from among Cu and Zn.

In a preferred embodiment of the process of the invention for producing a shaped catalyst body, the metal carbonate mixture comprised in the metal carbonate-comprising composition comprises, based on the total weight of the metal carbonate mixture,
   from 40 to 65% by weight of copper carbonate,
   from 35 to 60% by weight of zinc carbonate and
   from 0 to 20% by weight of a metal carbonate different from copper carbonate and zinc carbonate.

The copper carbonate comprised in the metal carbonate mixture is usually basic copper carbonate, i.e. copper hydroxycarbonate, for example $[Cu(CO_3)]\cdot[Cu(OH)_2]$ and/or $2[Cu(CO_3)]\cdot[Cu(OH)_2]$.

The zinc carbonate comprised in the metal carbonate mixture is usually zinc carbonate, for example $Zn(CO_3)$ and/or $Zn_2(CO_3)$, and/or basic zinc carbonate, i.e. zinc hydroxycarbonate, for example $2[Zn(CO_3)]\cdot3[Zn(OH)_2]$.

The metal carbonate which is different from copper carbonate and zinc carbonate is preferably selected from among cobalt carbonate, nickel carbonate, gold carbonate, cadmium carbonate, ruthenium carbonate and iron carbonate.

The metal carbonate mixture used in the present invention can comprise further metal compounds different from metal carbonates, in particular metal salts different from metal carbonates, as impurities or/and one or more metal compound(s) different from metal carbonates, in particular (a) metal salt(s) different from metal carbonates, can be added to the metal carbonate mixture. If one or more metal compound(s) different from metal carbonates, in particular one or more metal salt(s) different from metal carbonates, is/are added to the metal carbonate mixture, the proportion of this/these in the total weight of the metal carbonate mixture is not more than 25% by weight, preferably not more than 15% by weight, particularly preferably not more than 10% by weight and in particular not more than 5% by weight.

The metal compounds which are different from metal carbonates and can be comprised as impurities in the metal carbonate mixture are usually metal salts different from metal carbonates which are used as starting materials for producing the metal carbonates. These are frequently the nitrates, halides, for example the chlorides, bromides and/or iodides, oxides, hydroxides, acetates, phosphates and/or sulfates of Co, Ni, Cu, Au, Zn, Cd, Ru, Fe, Ca, Ba, Ce, Ti, Zr, Cr, Mo, Mn, Sn, Al, Si, or mixtures thereof.

In this context, the term "impurity/impurities" means that the amount of the abovementioned metal compounds different from metal carbonates in the metal carbonate mixture is not more than 1% by weight, preferably not more than 0.5% by weight, in particular not more than 0.1% by weight, based on the total weight of the metal carbonate mixture.

If one or more metal compound(s) different from metal carbonates is/are added to the metal carbonate mixture, the metal compound(s) different from metal carbonates which is/are added is/are preferably selected from among nitrates, halides, for example the chlorides, bromides and/or iodides, oxides, hydroxides, acetates, phosphates and sulfates of Ca, Ba, Ce, Ti, Zr, Cr, Mo, Mn, Sn, Al and Si, in particular from among nitrates, halides, for example the chlorides, bromides and/or iodides, oxides and sulfates of Ce, Zr, Mn and Al.

In particular, no further metal compound different from metal carbonates is added to the metal carbonate mixture used in the present invention. Of course, small amounts of metal compounds different from metal carbonates, especially metal salts different from metal carbonates as defined above, can nevertheless be comprised as impurities in the metal carbonate mixture used in the present invention.

In general, the amount of metal carbonates as defined above in the metal carbonate mixture is 75% by weight or more, preferably 85% by weight or more, based on the total weight of the metal carbonate mixture.

In particular, the amount of metal carbonates as defined above in the metal carbonate mixture is 90% by weight or more, for example 95% by weight or 97% by weight, based on the total weight of the metal carbonate mixture.

In a particularly preferred embodiment of the process of the invention for producing a shaped catalyst body, the metal carbonate mixture comprised in the metal carbonate-comprising composition consists of
from 40 to 65% by weight of copper carbonate and
from 35 to 60% by weight of zinc carbonate.

In this particularly preferred embodiment, too, the metal carbonate mixture can nevertheless comprise small amounts of copper compounds and zinc compounds different from copper carbonate and zinc carbonate, especially copper salts and zinc salts different from copper carbonate and zinc carbonate, as impurities.

If copper carbonate and zinc carbonate is comprised in the metal carbonate mixture or the metal carbonate mixture consists of copper carbonate and zinc carbonate, the molar ratio of copper carbonate and zinc carbonate in the metal carbonate mixture is usually in the range from 2:1 to 1:1.5, preferably in the range from 1.7:1 to 1:1.2, in particular in the range from 1.5:1 to 1:1.

In a further preferred embodiment of the process of the invention for producing a shaped catalyst body, the metal carbonate mixture comprised in the metal carbonate-comprising composition comprises, based on the total weight of the metal carbonate mixture,
from 22 to 37% by weight of copper and
from 18 to 33% by weight of zinc.

The metal carbonate mixture comprised in the metal carbonate-comprising composition particularly preferably comprises, based on the total weight of the metal carbonate mixture,
from 25 to 34% by weight of copper and
from 20 to 30% by weight of zinc.

The copper and zinc comprised in the metal carbonate mixture is predominantly present as copper carbonate and zinc carbonate as defined above. In addition, the copper and zinc comprised in the metal carbonate mixture can also be present in the form of metal salt(s) different from metal carbonates in the amounts indicated above for impurities.

In this preferred embodiment, not more than 15% by weight, preferably not more than 10% by weight, particularly preferably not more than 5% by weight, of a metal different from copper and zinc can be comprised in the form of one or more metal carbonates and/or in the form of a metal salt different from metal carbonates in the metal carbonate mixture. The metal different from copper and zinc is preferably selected from among Co, Ni, Au, Cd, Ru and Fe.

In particular, the metal carbonate mixture does not comprise any further metals different from copper and zinc, apart from the abovementioned impurities.

If the metal carbonate mixture comprised in the metal carbonate-comprising composition comprises copper and zinc, the molar ratio of copper and zinc in the metal carbonate mixture is preferably in the range from 2:1 to 1:1.5, particularly preferably in the range from 1.7:1 to 1:1.2 and in particular in the range from 1.5:1 to 1:1.

Accordingly, in a further particularly preferred embodiment of the process of the invention the metal carbonate-comprising composition provided in step a) comprises, based on the total weight of the metal carbonate-comprising composition,
from 70 to 94.5% by weight of a metal carbonate mixture comprising from 2 to 10 metal carbonates of from 2 to 10 different metals (M),
from 5 to 25% by weight of metallic copper and
from 0.5 to 5% by weight of tableting aid,
where the metal carbonate mixture comprised in the metal carbonate-comprising composition comprises copper and zinc and the molar ratio of copper and zinc in the metal carbonate mixture is in the range from 2:1 to 1:1.5.

According to the invention, the metal carbonate-comprising composition provided in step a) additionally comprises from 5 to 25% by weight, preferably from 7 to 20% by weight, in particular from 10 to 15% by weight, of metallic copper. The metallic copper is usually added in a form suitable for mixing and pressing, for example copper powder or copper flakes, to the metal carbonate-comprising composition.

The metallic copper is preferably copper powder and/or copper flakes.

Furthermore, the metal carbonate-comprising composition provided in step a) additionally comprises from 0.5 to 5% by weight, preferably from 0.5 to 4% by weight, in particular from 1 to 3% by weight, of tableting aid.

The tableting aid usually comprises compounds which reduce the friction occurring during shaping, for example oils, stearates, graphite, boron nitride or molybdenum disulfide.

The tableting aid is preferably selected from among graphite, boron nitride, molybdenum disulfide and mixtures thereof.

In a preferred embodiment of the process of the invention for producing a shaped catalyst body, a metal carbonate-comprising composition which comprises, based on the total weight of the metal carbonate-comprising composition,
  from 76 to 92.5% by weight of a metal carbonate mixture comprising from 2 to 10 metal carbonates of from 2 to 10 different metals (M),
  from 7 to 20% by weight of metallic copper and
  from 0.5 to 4% by weight of tableting aid
is provided in step a).

In a further preferred embodiment of the process of the invention for producing a shaped catalyst body, a metal carbonate-comprising composition which comprises, based on the total weight of the metal carbonate-comprising composition,
  from 76 to 92.5% by weight of a metal carbonate mixture comprising from 2 to 10 metal carbonates of from 2 to 10 different metals (M),
  from 7 to 20% by weight of metallic copper and
  from 0.5 to 4% by weight of tableting aid
is provided in step a),
  where the metal carbonate mixture comprised in the metal carbonate-comprising composition comprises, based on the total weight of the metal carbonate mixture,
  from 22 to 36% by weight of copper and
  from 18 to 33% by weight of zinc.

In a particularly preferred embodiment of the process of the invention for producing a shaped catalyst body, a metal carbonate-comprising composition which comprises, based on the total weight of the metal carbonate-comprising composition,
  from 82 to 89% by weight of a metal carbonate mixture comprising from 2 to 5 metal carbonates of from 2 to 5 different metals (M),
  from 10 to 15% by weight of metallic copper and
  from 1 to 3% by weight of tableting aid
is provided in step a).

In a further particularly embodiment of the process of the invention for producing a shaped catalyst body, a metal carbonate-comprising composition which comprises, based on the total weight of the metal carbonate-comprising composition,
  from 82 to 89% by weight of a metal carbonate mixture comprising from 2 to 5 metal carbonates or from 2 to 5 different metals (M),
  from 10 to 15% by weight of metallic copper and
  from 1 to 3% by weight of tableting aid
is provided in step a),
  where the metal carbonate mixture comprised in the metal carbonate-comprising composition comprises, based on the total weight of the metal carbonate mixture,
  from 22 to 36% by weight of copper and
  from 18 to 33% by weight of zinc.

In a specific embodiment of the process of the invention for producing a shaped catalyst body, a metal carbonate-comprising composition which comprises, based on the total weight of the metal carbonate-comprising composition,
  from 82 to 89% by weight of a metal carbonate mixture comprising from 40 to 65% by weight of copper carbonate, from 35 to 60% by weight of zinc carbonate and from 0 to 20% by weight of a metal carbonate which is different from copper carbonate and zinc carbonate,
  from 10 to 15% by weight of metallic copper and
  from 1 to 3% by weight of tableting aid
is provided in step a).

In a further specific embodiment of the process of the invention for producing a shaped catalyst body, a metal carbonate-comprising composition which comprises, based on the total weight of the metal carbonate-comprising composition,
  from 82 to 89% by weight of a metal carbonate mixture comprising, based on the total weight of the metal carbonate mixture, from 22 to 36% by weight of copper,
  from 18 to 33% by weight of zinc and from 0 to 15% by weight of a metal different from copper and zinc,
  from 10 to 15% by weight of metallic copper and
  from 1 to 3% by weight of tableting aid
is provided in step a).

In a very specific embodiment of the process of the invention for producing a shaped catalyst body, a metal carbonate-comprising composition which comprises, based on the total weight of the metal carbonate-comprising composition,
  from 82 to 89% by weight of a metal carbonate mixture consisting of from 40 to 65% by weight of copper carbonate and from 35 to 60% by weight of zinc carbonate,
  from 10 to 15% by weight of metallic copper and
  from 1 to 3% by weight of tableting aid
is provided in step a).

In a further very specific embodiment of the process of the invention for producing a shaped catalyst body, a metal carbonate-comprising composition which comprises, based on the total weight of the metal carbonate-comprising composition,
  from 82 to 89% by weight of a metal carbonate mixture comprising, based on the total weight of the metal carbonate mixture, from 22 to 36% by weight of copper and from 18 to 33% by weight of zinc,
  from 10 to 15% by weight of metallic copper and
  from 1 to 3% by weight of tableting aid
is provided in step a),
  where the metal carbonate mixture comprised in the metal carbonate-comprising composition does not comprise any further metals different from copper and zinc, apart from impurities.

According to the invention, the provision of the metal carbonate-comprising composition in step a) comprises the following steps
a1) provision of a pulverulent metal carbonate mixture comprising two or more than two metal carbonates of two or more than two different metals (M) and
a2) addition of the metallic copper and of the tableting aid to the pulverulent metal carbonate mixture provided in step a1).

According to the invention, the provision of the pulverulent metal carbonate mixture is carried out by customary methods known in the prior art for producing metal carbonates and/or metal carbonate mixtures.

The production of the metal carbonate mixture is preferably carried out in a manner analogous to the process described in DE 102014004413. In this context, the disclosure of DE 102014004413 is fully incorporated by reference.

Accordingly, the procedure comprises firstly forming a metal carbonate-comprising precipitate by combining a solution A and a solution B. The precipitate is then separated off from the liquid fraction of the combined solutions and washed. The precipitate which has been separated off is subsequently dried by heating to a temperature in the range from 75° C. to 140° C.

The solution A is produced by dissolving two or more than two metal compounds of two or more than two different metals (M) in a suitable solvent in a vessel.

As an alternative, the two or more than two metal compounds of two or more than two different metals (M) can be dissolved in a plurality of vessels and the solutions obtainable therefrom can be combined to give a solution A.

The solution B is produced by dissolving a carbonate compound in a suitable solvent.

In this context, the expressions "solutions A" and "solutions B" used here include both solutions and also suspensions and slurries, with preference being given to solutions.

The solvent is preferably water. An acid or base can be added to the water in order to assist dissolution of the compounds. The water can, for example, have a neutral pH of about 7, an acidic pH of from about 0 to less than 7, or a basic pH of from greater than 7 to about 14.

As a person skilled in the art will know, a pH suitable for dissolving the compounds is selected as a function of the compound to be dissolved. The water usually has a pH in the range from 4 to 10, preferably from 5 to 9.

As metal compounds, it is in principle possible to use both the respective metals in metallic form or preferably all compounds of the respective metals (M), as defined above, which are readily soluble in water, acids or alkalis.

The metal compounds of two or more than two different metals (M) which are used for producing the solution A are particularly preferably selected from among the nitrates, carbonates, hydroxycarbonates, hydrogencarbonates, halides, for example the chlorides, bromides and/or iodides, oxides, hydroxides, acetates, amine complexes, phosphates, sulfites and sulfates of the metals (M), as defined above.

If oxides of the metals (M), for example copper oxide and/or zinc oxide, are used for producing the aqueous solutions, these are preferably partly or completely dissolved by addition of a suitable mineral acid. The mineral acid is preferably selected from among $HNO_3$, HCl, $H_2SO_4$ and mixtures thereof. If copper oxide is used as metal oxide, the copper in the copper oxide can be present in one or more different oxidation states, e.g. copper(I) oxide, copper(II) oxide and mixtures thereof. If the metals, for example copper and/or zinc, are themselves used for producing the aqueous solution(s), suspension(s) or slurry/slurries, these are preferably partly or completely dissolved by addition of suitable acids or alkalis. The dissolution of the metals can, for example, be effected in inorganic acids or alkalis.

The metal compounds of two or more than two different metals (M) which are used for producing the solution A are very particularly preferably selected from among the nitrates, carbonates, hydroxycarbonates, hydrogencarbonates, chlorides, bromides, hydroxides and sulfates of Co, Ni, Cu, Au, Zn, Cd, Ru and Fe.

In particular, the metal compounds of two or more than two different metals (M) which are used for producing the solution A are selected from among the nitrates, carbonates, hydroxycarbonates, hydrogencarbonates, chlorides and sulfates of Ni, Cu, Au and Zn.

If a copper compound is used as metal compound for producing the solution A, this is preferably selected from among copper oxide ($Cu_2O$ and/or CuO), copper nitrate, copper chloride, copper carbonate and copper hydroxycarbonate, as defined above, Cu-amine complexes (e.g. copper tetrammine complexes ($[Cu(NH_3)_4]^{2+}$) or copper hexamine complexes ($[Cu(NH_3)_6]^{2+}$), which can, for example, be used as chloride, hydroxide or sulfate), copper acetate and copper sulfate, particularly preferably from among copper nitrate, copper chloride and copper sulfate. As an alternative, copper metal can also be dissolved in oxidizing acids such as nitric acid ($HNO_3$).

If a zinc compound is used as metal compound for producing the solution A, this is preferably selected from among zinc nitrate, zinc sulfate, zinc chloride, zinc carbonate, zinc hydroxide, zinc sulfite, zinc acetate and zinc phosphate, in particular from among zinc nitrate, zinc chloride and zinc sulfate. As an alternative, zinc metal or ZnO can also be dissolved in acids such as hydrochloric acid (HCl) or nitric acid ($HNO_3$) or in alkalis such as sodium hydroxide (NaOH) or potassium hydroxide (KOH).

In particular, the metal compounds used for producing the solution A are copper sulfate and zinc sulfate.

The carbonate compounds used for producing the solution B are preferably selected from among alkali carbonates such as lithium carbonate, sodium carbonate, potassium carbonate, rubidium carbonate and cesium carbonate, alkaline earth metal carbonates such as magnesium carbonate, calcium carbonate, strontium carbonate and barium carbonate, ammonium carbonate or mixtures thereof. Likewise, the corresponding hydrogencarbonates or any mixtures of carbonates and hydrogencarbonates can be used together with or instead of the carbonates.

Preference is given to using alkali metal carbonates, ammonium carbonates, alkali metal hydrogencarbonates, ammonium hydrogencarbonates or mixtures thereof, particularly preferably alkali metal carbonates and/or alkali metal hydrogencarbonates.

Preferred alkali metal carbonates are sodium carbonate and potassium carbonate, in particular sodium carbonate. Preferred alkali metal hydrogencarbonates are sodium hydrogencarbonate and potassium hydrogencarbonate, in particular sodium hydrogencarbonate. Particular preference is given to using sodium carbonate and/or sodium hydrogencarbonate.

The combining is usually carried out by introducing the solution A and solution B simultaneously into a common vessel, for example a precipitation vessel. Here, the two solutions are preferably introduced continuously into the reaction volume of a precipitation mixer. In a further embodiment, combining can also be carried out by adding the solution A or solution B to the associated other solution B or solution A present, for example, in a vessel such as a precipitation vessel. In a preferred embodiment, the combining of the solutions is effected by adding the solution A to the carbonate-comprising solution B present in a precipitation vessel.

The solution A can optionally be heated to a temperature of 20° C. or more, for example to a temperature in the range from 25° C. to 90° C., and preferably stirred before combining of the solutions. The solution A is preferably not heated before combining of the solutions.

The solution B can optionally be heated to a temperature of 20° C. or more, for example to a temperature in the range from 25° C. to 90° C., and preferably stirred before combining of the solutions. The solution B is preferably not heated before combining of the solutions.

During the combining of the solution A and solution B, a metal carbonate-comprising precipitate, which is usually present as suspension, is formed. Combining of the solutions is generally carried out in a stirred vessel. The vessel is preferably stirred by means of an inclined-blade stirrer, propeller stirrer or another commercial stirrer.

The suspension of the metal carbonate-comprising precipitate obtained after combining of the solution A and solution B is usually heated to a temperature of 20° C. or more, for example to a temperature in the range from 25° C. to 90° C., in particular in the range from 30° C. to 70° C., and stirred for from a few minutes to some hours, for example for from 5 minutes to 5 hours, in particular for from 20 minutes to 2 hours.

The metal carbonate-comprising precipitate is preferably separated off by filtration. As an alternative, the precipitate can also be separated off by decantation or centrifugation.

The precipitate which has been separated off is subsequently subjected to one or more washing steps. Here, it is possible for the precipitate-comprising solution mixture firstly to be separated from the precipitate by use of a filterpress and water subsequently to be passed through the material in the filterpress and the material being washed thereby. As an alternative, the precipitate which has been separated off can, after the precipitate-comprising solution mixture has been separated off by filtration, decantation or centrifugation, be slurried in a vessel and subsequently be separated again from the liquid phase by means of a filterpress, a centrifuge or a decanter. This operation is generally carried out one or more times until a particular conductivity of the filtrate has been reached.

The isolated and washed precipitate is subsequently subjected to drying. Drying is effected by heating the precipitate to a temperature in the range from 75° C. to 140° C., preferably in the range from 90° C. to 130° C. Drying can, for example, be carried out by spray drying or by drying in a drying oven.

Drying can be carried out at ambient pressure or under reduced pressure. Drying is preferably carried out at ambient pressure.

The metal carbonate mixture obtained in this way is subsequently milled to a powder if it is not already in suitable powder form as a result of the manner of drying, as is usually the case for spray drying, and optionally sieved to a desired particle size, for example a particle size in the range from 0.1 to 2 mm, preferably in the range from 0.3 to 1.6 mm. One or more metal compound(s) different from metal carbonates, as defined above, are optionally additionally added in a form suitable for mixing and pressing, for example in the form of a powder, to the metal carbonate mixture.

Metallic copper in a form suitable for mixing and pressing, for example in the form of copper powder or copper flakes, and the tableting aid, likewise in a form suitable for mixing and pressing, for example in the form of a powder, are then added in the above-described amounts to the pulverulent metal carbonate mixture (step a2)).

Step b) of the Process

The metal carbonate-comprising composition provided in this way in step a) is subsequently shaped to give a shaped body.

For this purpose, it is possible to use all shaping methods known to those skilled in the art. Shaping is preferably effected by pressing or tableting of the metal carbonate-comprising composition provided in step a) to give the desired shaped bodies.

The shaped bodies are preferably free-flowing particles having a maximum diameter in the range from 1 to 20 mm, for example granules or pellets. The shaped bodies are particularly preferably pellets having a diameter in the range from 1 to 10 mm and a height in the range from 1 to 10 mm, preferably having a diameter in the range from 1.5 to 5 mm and a height in the range from 1.5 to 5 mm.

Tableting is preferably carried out by means of a tableting press, for example a Kilian E150 Plus tableting press.

After tableting, the pellets usually have a lateral compressive strength, measured in accordance with DIN EN 1094-5, of at least 10 N, preferably at least 20 N, in particular at least 25 N, especially from 25 to 110 N, very especially from 25 to 90 N, and a bulk density in the range from 1.1 to 2.2 g/ml, preferably in the range from 1.2 to 2.0 g/ml, in particular in the range from 1.3 to 1.9 g/ml.

The pellets produced by the tableting operation preferably have a diameter in the range from 1.5 to 5 mm, a height in the range from 1.5 to 5 mm and a lateral compressive strength of at least 25 N, especially from 25 to 110 N, very especially from 25 to 90 N.

After shaping and before activation in step c), the shaped catalyst bodies comprise a carbonate content in the range from 15 to 45% by weight.

The shaped catalyst bodies after shaping and before activation in step c) preferably comprise a carbonate content in the range from 15 to 45% by weight, particularly preferably from 17 to 40% by weight, in particular from 20 to 35% by weight.

The carbonate content, in particular that of the shaped catalyst body or the metal carbonate-comprising composition, is for this purpose determined by a method analogous to the method described in F. Ehrenberger: "Quantitative Organische Elementaranalyse", VCN Verlagsgesellschaft mbH, Weinheim; 1991 edition; ISBN: 3-527-28056-1, pages 225 ff.

Afterwards, the inorganic carbon comprised in the respective sample of the shaped catalyst body or the metal carbonate-comprising composition, which is usually present in the form of carbonate, hydroxycarbonate and/or hydrogencarbonate ions, is converted with introduction of a little heat by means of dilute phosphoric acid into carbonic acid which decomposes into $CO_2$ and $H_2O$. The $CO_2$ which has been liberated in this way is driven off from the sample by means of a stream of inert gas. Undesirable components are removed in a subsequent gas scrub. The content of $CO_2$ in the inert gas stream is subsequently quantified by means of infrared-spectroscopic measurement. In this method, the smallest amount of inorganic carbon which can still be determined reliably in a sample is about 1 mg of inorganic carbon per 100 g of sample.

In a first embodiment of the process of the invention for producing a shaped catalyst body, the shaped body obtained in step b) is subsequently passed directly to activation (step c)).

Step c) of the Process

In step c) of the process of the invention, the shaped body obtained in step b) is activated at a temperature in the range from 150 to 250° C. in the presence of hydrogen, i.e. in the presence of a reducing atmosphere.

For the purposes of the present patent application, the expression "in the presence of hydrogen" means that the activation is carried out under a hydrogen atmosphere or under a hydrogen-comprising atmosphere. Alternatively, the expression "in the presence of hydrogen" also means that hydrogen or a hydrogen-comprising gas is passed through the shaped bodies obtained in step b).

The activation is preferably carried out by passing hydrogen or a hydrogen-comprising gas, preferably a hydrogen-comprising gas, through the shaped bodies obtained in step b).

The hydrogen-comprising gas is, for the purposes of the present invention, a gas mixture which consists of one or more inert gas(es) and from 0.1% by volume to 99.9% by volume of hydrogen.

If a hydrogen-comprising gas is passed through the shaped bodies obtained in step b) to effect activation, the concentration of hydrogen in the hydrogen-comprising gas can be kept constant or slowly increased over the course of the activation, for example from about 0.1% by volume to about 99.9% by volume. For example, a mixture consisting of hydrogen and one or more inert gas(es) can be passed through the shaped bodies to effect activation, with the ratio of hydrogen to the inert gas(es) being about 0.1% by volume of hydrogen to 99.9% by volume of inert gas(es) at the beginning. The ratio of hydrogen to the inert gas(es) is then gradually increased (e.g. continuously or stepwise) until finally gas comprising, for example, 99.9% by volume of hydrogen is passed through the shaped catalyst bodies, with pure hydrogen also being able to be passed through the shaped catalyst bodies at the end. This procedure usually takes place under temperature control. In this context, the expression "under temperature control" means that the proportion of hydrogen in the hydrogen-comprising gas is increased in such a way that the temperature of the shaped catalyst body does not exceed 300° C., preferably 250° C., and is in particular in the range from 150 to 250° C.

If the concentration of hydrogen in the hydrogen-comprising gas is kept constant during activation, the hydrogen-comprising gas is a gas mixture which consists of one or more inert gas(es) and at least 5% by volume, preferably at least 10% by volume, in particular from 10 to 95% by volume, of hydrogen.

The concentration of hydrogen in the hydrogen-comprising gas is preferably slowly increased over the course of the activation, as defined above.

The expression "inert gas" used in the context of the present invention refers to gases which do not undergo any reactions with the shaped catalyst body under the given process conditions. The inert gas is usually selected from among nitrogen and noble gases, for example helium or argon, and the inert gas is preferably selected from among nitrogen and argon. In particular, the inert gas is nitrogen.

The activation is preferably carried out at a temperature in the range from 170° C. to 240° C., in particular in the range from 190° C. to 210° C. The duration of the activation is dependent on the amount of catalyst to be reduced and can therefore vary greatly. For example, the activation of an amount of catalyst in the range from 10 to 1000 g is carried out over a time of from 0.5 to 2 hours. In the case of amounts of catalyst in the range from 10 kg to 1000 kg, the activation is, for example, carried out over a time of from 4 hours to 3 days.

If the activation is carried out under a hydrogen atmosphere or under a hydrogen-comprising atmosphere, the activation can be carried out at ambient pressure or under an elevated pressure, for example under a pressure in the range from 1.1 to 250 bar.

The activation is preferably carried out at ambient pressure.

In a second embodiment of the process of the invention for producing a shaped catalyst body, the shaped body obtained in step b) is firstly subjected, in a step c1), to a first thermal treatment at a temperature in the range from 150 to 350° C. in the absence of hydrogen. The shaped body which has been thermally treated in this way is subsequently activated at a temperature in the range from 150 to 250° C. in the presence of hydrogen in a step c2).

Step c1)

The first thermal treatment in the absence of hydrogen is generally carried out at a temperature in the range from 150 to 350° C., preferably in the range from 180 to 310° C., particularly preferably in the range from 200 to 300° C., in particular in the range from 200 to 250° C.

According to the invention, the thermal treatment is carried out in the absence of hydrogen. This means that the thermal treatment is carried out under air or under an inert gas, as defined above, or under a mixture of air with an inert gas. The thermal treatment is preferably carried out under air.

The shaped catalyst bodies, in particular the catalyst pellets, obtained after the thermal treatment usually have a lateral compressive strength, measured in accordance with DIN EN 1094-5, of at least 5 N, preferably at least 10 N, in particular at least 15 N, especially from 15 to 90 N, very especially from 15 to 80 N, and a bulk density in the range from 0.8 to 1.6 g/ml, preferably in the range from 0.9 to 1.5 g/ml, in particular in the range from 1.0 to 1.4 g/ml.

The shaped catalyst bodies, in particular the catalyst pellets, obtained after the thermal treatment preferably have a diameter in the range from 1.5 to 5 mm, a height in the range from 1.5 to 5 mm and a lateral compressive strength of at least 15 N, especially from 15 to 90 N, very especially from 15 to 80 N.

The shaped catalyst bodies of this second embodiment obtained after the thermal treatment and before the activation in step c2) usually have a carbonate content in the range from 0.1 to 2.5% by weight.

The shaped catalyst bodies of this second embodiment obtained after the thermal treatment and before the activation in step c2) preferably have a carbonate content in the range from 0.2 to 2.3% by weight, in particular from 0.4 to 2.1% by weight.

Step c2)

In the second embodiment of the process of the invention, the thermally treated shaped bodies are subsequently activated at a temperature in the range from 150 to 250° C. in the presence of hydrogen in a step c2).

The activation in step c2) is carried out in a manner analogous to step c) of the first embodiment. As regards the procedure for step c2), reference is made to what has been said above under step c).

In a preferred embodiment of the process of the invention for producing a shaped catalyst body, the shaped catalyst body is passivated at a temperature of 60° C. or less in the presence of an oxygen-comprising gas mixture, in particular air, after the activation in step c) or c2).

In this context, the term "oxygen-comprising gas mixture" refers to air and also to gas mixtures of oxygen or air with an inert gas.

In the passivation, air or a mixture of oxygen or air and an inert gas, e.g. argon or nitrogen, is fed into the reduction reactor.

If the passivation is carried out in the presence of a mixture of oxygen or air and an inert gas, e.g. argon or nitrogen, the concentration of oxygen in the mixture can be kept constant or be slowly increased over the course of the passivation, for example from about 0.04% by volume to about 21% by volume. For example, a mixture of air and inert gas can be fed in, with the ratio of air to inert gas being about 0.2% by volume of air to 99.8% by volume of inert gas at the beginning. The ratio of air to inert gas is then gradually increased (e.g. continuously or stepwise) until finally 100% by volume of air, for example, is fed in (which corresponds to an oxygen concentration of about 21% by volume).

The passivation is preferably carried out in the presence of air.

The passivation is usually carried out at a temperature of 60° C. or less. The passivation is preferably carried out at a temperature in the range from 5 to 55° C., particularly preferably in the range from 10 to 50° C., in particular in the range from 15 to 45° C.

If the activation of the shaped body obtained in step b) is carried out in-situ in the hydrogenation reactor, passivation can generally be dispensed with.

The shaped catalyst bodies obtained by means of the above-described production process according to the invention have not only a significantly increased strength but also an increased hydrogen activity compared to conventional shaped catalyst bodies which have been produced from the same metal carbonate mixture but without the addition of metallic copper.

For this reason, the present invention further provides shaped catalyst bodies which are obtainable by the above-described production process.

The shaped catalyst bodies, in particular the catalyst pellets, obtained by the above-described production process according to the invention, i.e. after activation according to one of the steps c) or c2) and optionally subsequent passivation, usually have a lateral compressive strength, measured in accordance with DIN EN 1094-5, of at least 5 N, preferably at least 10 N, in particular at least 15 N, especially from 15 to 60 N, very especially from 15 to 50 N, and a bulk density in the range from 0.8 to 1.6 g/ml, preferably in the range from 0.9 to 1.5 g/ml, in particular in the range from 1.0 to 1.4 g/ml.

The shaped catalyst bodies, in particular the catalyst pellets, obtained by the above-described production process according to the invention, i.e. after the activation according to one of the steps c) or c2) and optionally subsequent passivation, preferably have a diameter in the range from 1.5 to 5 mm, a height in the range from 1.5 to 5 mm and a lateral compressive strength of at least 15 N, especially from 15 to 60 N, very especially from 15 to 50 N.

Hydrogenation

Owing to their high hydrogenation activity, the shaped catalyst bodies of the invention are advantageous for use in hydrogenation reactions. The shaped catalyst bodies of the invention are preferably suitable for the hydrogenation of an organic compound having one or more than one carbonyl group(s).

The hydrogenation of an organic compound having one or more than one carbonyl group(s) is, for example, the hydrogenation of esters, in particular fatty acid esters, the hydrogenation of diesters (in particular diesters of maleic acid) to form diols, the hydrogenation of sugars to form polyols, the hydrogenation of an aldehyde, the hydrogenation of an amide, the hydrogenation of a fatty acid (e.g. by esterification and subsequent hydrogenolysis), the selective hydrogenation of a fat, the selective hydrogenation of an oil, the hydrogenation of a nitroaromatic hydrocarbon, the hydrogenation of a ketone, the hydrogenation of furfural and the hydrogenation of carbon monoxide or carbon dioxide to form methanol.

Accordingly, the present invention further provides a process for the hydrogenation of an organic compound having one or more than one carbonyl group(s), in which the organic compound is brought into contact in the presence of hydrogen with a shaped catalyst body obtainable by the above-described process.

The organic compound having one or more than one carbonyl group(s) preferably comprises aldehydes, ketones, carboxylic acids, e.g. monocarboxylic, dicarboxylic, tricarboxylic and tetracarboxylic acids, and ester compounds, e.g. monoesters, diesters, triesters and tetraesters, particularly preferably ester compounds such as monoesters, diesters, triesters and tetraesters.

In particular, the organic compound having one or more than one carbonyl group(s) comprises $C_8$-$C_{24}$-fatty acid alkyl esters, especially $C_8$-$C_{24}$-fatty acid methyl esters, very especially $C_{10}$-$C_{18}$-fatty acid methyl esters.

The organic compounds having one or more than one carbonyl group(s), in particular the $C_8$-$C_{24}$-fatty acid alkyl esters, used in the hydrogenation can be present as individual compounds or as mixtures, in particular as $C_8$-$C_{24}$-fatty acid alkyl ester mixtures. If esters, in particular a $C_8$-$C_{24}$-fatty acid alkyl ester, or mixtures of esters, in particular mixtures of $C_8$-$C_{24}$-fatty acid alkyl esters, are used in the hydrogenation, these can additionally comprise the corresponding carboxylic acid(s), in particular the corresponding $C_8$-$C_{24}$-fatty acid(s). The esters, in particular the $C_8$-$C_{24}$-fatty acid alkyl esters, used in the hydrogenation preferably do not comprise any corresponding carboxylic acid(s).

The hydrogenation can be carried out in a manner analogous to known hydrogenation processes for the catalytic hydrogenation of organic compounds having carbonyl groups.

Here, the organic compound having one or more than one carbonyl group(s) which is to be hydrogenated is brought into contact, usually in liquid or gaseous form, preferably in liquid form, with the shaped catalyst bodies of the invention in the presence of hydrogen in one or more hydrogenation reactors, preferably in one hydrogenation reactor. The liquid phase can be passed over a fluidized bed or fixed bed consisting of the shaped catalyst bodies of the invention. The liquid phase is preferably passed downward or upward over a fixed bed consisting of the shaped catalyst bodies of the invention. The catalytic hydrogenation can be carried out continuously or batchwise. As hydrogenation reactors, it is possible to use all conventional reactors known in the prior art for the hydrogenation of organic compounds, for example a stirred reactor.

The hydrogenation is usually carried out under an elevated hydrogen pressure. The hydrogenation is preferably carried out at a hydrogen pressure in the range from 5 to 400 bar, in particular from 10 to 300 bar.

The hydrogenation is usually carried out at a temperature in the range from 30 to 350° C., in particular in the range from 50 to 300° C.

EXAMPLES

The following abbreviations are used in the examples below:
Soda is sodium carbonate.
LCS is lateral compressive strength.
BD is bulk density.
red/pass means reduced and passivated.

Examples 1 and 4.1 are comparative examples (which are not according to the invention). The other examples are according to the invention.

Example 1 (for Comparison)

Production of Catalyst Pellets without Addition of Copper

Production of a Metal Carbonate Mixture

A mixture of 12 kg of a 20% strength by weight aqueous copper sulfate solution (1.25 mol of $CuSO_4$/kg of solution) and 10 kg of a 20% strength by weight aqueous zinc sulfate solution (1.24 mol of $ZnSO_4$/kg of solution) is added while stirring to 13.5 kg of a 20% strength by weight soda solution having a temperature of 20° C. (1.89 mol of $Na_2CO_3$/kg of solution) until the pH has decreased from an initial 12 to 7.2. The suspension is then heated to 50° C. and stirred further for one hour, during which time the pH decreases further to a small extent down to a pH of 7.0. The suspension is cooled, filtered and washed until sulfate-free (<0.1%). Drying is subsequently carried out overnight at 120° C. in a drying oven.

The dry Cu—Zn carbonate mixture obtained in this way comprises, based on the total weight of the metal carbonate mixture, 29% by weight of Cu and 25% by weight of Zn.

The copper and zinc contents were determined by means of elemental analysis using atomic absorption spectrometry.

Tableting

The dry metal carbonate mixture is milled to a metal carbonate powder, sieved to from 0.4 to 1.5 mm and mixed with 2% by weight of graphite. This is followed by shaping to give pellets having a diameter of 3 mm and a height of 3 mm. "Green" pellets having a lateral compressive strength of 32 N and a bulk density of 1.2 g/ml result. Reduction at 200° C. in a stream of $H_2$ and subsequent passivation at 30° C. under air results in pellets having a lateral compressive strength (LCS) which has been reduced to 9 N and a bulk density (BD) of 0.95 g/ml and a pellet diameter which has shrunk to 2.85 mm (catalyst 1). The decreasing mass during the reduction operation is 30% by weight.

Example 2: Production of Catalyst Pellets With Addition of 15% by Weight of Copper The production of the metal carbonate mixture is carried out in a manner analogous to example 1. The dry metal carbonate mixture is milled to a metal carbonate powder, sieved to from 0.4 to 1.5 mm and mixed with 2% by weight of graphite and 15% by weight of copper powder (Unicoat copper 3845). This is followed by shaping to give pellets having a diameter of 3 mm and a height of 3 mm. "Green" pellets having a lateral compressive strength of 45 N and a bulk density of 1.72 g/ml result. The green pellets have a carbonate content of 20.4% by weight (determined as described in example 6). Reduction at 200° C. in a stream of $H_2$ and subsequent passivation at 30° C. under air results in pellets having a lateral compressive strength (LCS) which has been reduced to 21 N and a bulk density (BD) of 1.2 g/ml and a virtually unchanged pellet diameter of 2.99 mm (catalyst 2).

Example 3: Production of Catalyst Pellets With Addition of 15% by Weight of Copper and Preliminary Heat Treatment (Thermal Treatment)

The production of the metal carbonate mixture is carried out in a manner analogous to example 1. The dry metal carbonate mixture is milled to a metal carbonate powder, sieved to from 0.4 to 1.5 mm and mixed with 2% by weight of graphite and 15% by weight of copper powder (Unicoat copper 3845). This is followed by shaping to give pellets having a diameter of 3 mm and a height of 3 mm. "Green" pellets having a lateral compressive strength of 45 N and a bulk density of 1.72 g/ml result. The green pellets have a carbonate content of 20.4% by weight (determined as described in example 6). The pellets obtained in this way are then subjected to preliminary heat treatment at 250° C. for 2 hours. Reduction at 200° C. in a stream of $H_2$ and subsequent passivation at 30° C. under air results in pellets having a lateral compressive strength (LCS) which has been reduced to 20 N and a bulk density (BD) of 1.30 g/ml and a slightly decreased pellet diameter of 2.93 mm (catalyst 3).

Examples 4.1 to 4.4

Production of Catalyst Pellets With Addition of Various Amounts of Copper

Four different catalyst pellets were produced in a manner analogous to example 1 or example 2, with 0, 5, 10 and 15% by weight of copper powder being added before tableting. In the interests of better comparability, the machine parameters of the tableting press was selected so that all four catalyst pellet samples have a lateral compressive strength of about 30 N (measured as green pellets, i.e. the product coming directly from the tableting press).

All catalyst pellets were dried at 160° C., then reduced at 220° C. in a stream of $H_2$ and subsequently passivated at 30° C. under air.

The physical properties of the resulting catalyst pellets are summarized in table 1 below.

TABLE 1

Physical properties of catalyst pellets comprising different amounts of added copper

| Ex.: | Cu addition [% by weight] | Carbonate content*) [% by weight] | LCS of green bodies [N] | LCS after red. [N] | Diameter after red. [mm] | BD after red. [g/ml] |
|---|---|---|---|---|---|---|
| 4.1 **) | 0 | 24.2 | 32 | 9 | 2.85 | 0.95 |
| 4.2 | 5 | 22.9 | 32 | 9 | 2.92 | 0.98 |
| 4.3 | 10 | 22.0 | 32 | 17 | 2.94 | 1.08 |
| 4.4 | 15 | 20.9 | 31 | 19 | 2.97 | 1.16 |

*)Carbonate content of the green pellets (the product coming directly from the tableting press)
**) Example 4.1 is a comparative example (addition of 0% of Cu)

From these values, it is possible to see a significant effect in respect of the hardness and the bulk density of the catalyst pellets in the case of an addition of from 10 to 15% by weight of copper. Significantly harder and denser catalyst pellets can be produced by addition of copper.

Examples 5.1 to 5.5: Production of Catalyst Pellets Having an Addition of 15% by Weight of Copper and Preliminary Heat Treatment (Thermal Treatment) at Various Temperatures Catalyst Pellets having an addition of 15% by weight of copper were produced in a manner analogous to example 4.4, with the catalyst pellets obtained after tableting being subjected to preliminary heat treatment at 200, 250, 300 and 350° C., then reduced (activated) at 220° C. in a stream of $H_2$ and subsequently passivated at 30° C. under air.

The physical properties of the resulting catalyst pellets are summarized in Table 2 below.

TABLE 2

Physical properties of catalyst pellets with preliminary heat treatment (thermal treatment) at various temperatures.

| Ex.: | Temperature of preliminary heat treatment [° C.] | LCS after red. [N] | Diameter after red. [mm] | BD after red. [g/ml] |
|---|---|---|---|---|
| 5.1 | — | 19 | 2.97 | 1.12 |
| 5.2 | 200 | 23 | 2.87 | 1.15 |
| 5.3 | 250 | 22 | 2.89 | 1.17 |
| 5.4 | 300 | 17 | 2.88 | 1.21 |
| 5.5 | 350 | 16 | 2.89 | 1.14 |

From the values, it is possible to see a significant effect in respect of the hardness (LCS) and the bulk density of the catalyst pellets which have been subjected to a preliminary heat treatment at a temperature in the range of 200-300° C.

Example 6: Determination of the Carbonate Content of the Catalyst Pellets

The determination of the carbonate content is carried out in a manner analogous to the method described in F. Ehrenberger: "Quantitative Organische Elementaranalyse", VCN Verlagsgesellschaft mbH, Weinheim; 1991 edition; ISBN: 3-527-28056-1, page 225 ff.
Procedure
Apparatus Used:
IR module, e.g. from Dimatec
Microbalance, e.g. MT5/Analytical Balance AT261, from Mettler
Hotplate
Usual Laboratory Apparatus The inorganic carbon comprised in the respective sample of the shaped catalyst body or of the metal carbonate-comprising composition, which is usually present in the form of carbonate, hydroxycarbonate and/or hydrogencarbonate ions, is converted by means of dilute phosphoric acid with a small introduction of heat into carbonic acid which decomposes into $CO_2$ and $H_2O$. The $CO_2$ which has been liberated in this way is driven off from the sample by means of a stream of inert gas. In a subsequent gas scrub, undesirable components are removed. The content of $CO_2$ in the stream of inert gas is subsequently quantified by means of infrared-spectroscopic measurement. In this method, the smallest amount of inorganic carbon which can still be determined reliably in a sample is about 1 mg of inorganic carbon per 100 g of sample.

The weight of the sample was adapted in accordance with the expected content and the blank value of the system. The amount of catalyst sample used for determining the carbonate content was, depending on the determination limit required, from about 1 to 500 mg.

Example 7: Hydrogenation of $C_{10}$-$C_{18}$-Fatty Acid Methyl Esters

In a 300 ml Parr laboratory autoclave provided with a catalyst basket, 10 g in each case of the reduced and passivated (red/pass) catalyst and 200 ml of methyl ester are stirred at 220° C. and 170 bar of $H_2$ pressure for 5 hours in each case. The analytical results of the samples taken from the reaction mixture immediately after a reaction time of 5 hours are shown in table 3 below.

TABLE 3

Analytical results for the hydrogenation of $C_{10}$-$C_{18}$-fatty acid methyl esters using the catalysts from examples 1, 2 and 3.

| Example | 7.1 *) | 7.2 | 7.3 |
|---|---|---|---|
| Catalyst | 1 (from comparative example 1) | 2 (from example 2) | 3 (from example 3) |
| Fatty alcohols (%) | 71 | 74 | 75 |
| Methyl esters (%) | 14 | 12 | 12 |
| Wax esters (%) | 14 | 13 | 12 |
| Miscellaneous (%) | 1 | 1 | 1 |

*) comparative example

It can be seen that despite the use of the same amounts of catalyst, the catalysts 2 and 3 lead to at least the same activity as the comparative catalyst 1 (the activity even tends to be increased), even though these were "diluted" with in each case 15% of copper powder before tableting, i.e. 15% less active composition is thus available in these examples. In addition, these catalyst pellets which have been modified with copper powder display a significantly increased lateral compressive strength after reduction, which makes industrial use significantly easier.

For an assumed reactor volume of 1 m³, there are accordingly the following options (table 4):

TABLE 4

Use possibilites for the catalysts 1, 2 and 3 (catalysts from examples 1, 2 and 3) in a reactor having a volume of 1 m³.

| Catalyst | Mass of catalyst (in metric tons) | Proportion of "inert" copper (in metric tons) | Proportion of Cu/Zn after activation (in metric tons) |
|---|---|---|---|
| 1 (Green bodies) | 1.2 | — | 0.84 |
| 2 (red/pass) **) | 0.95 | — | 0.95 |
| 2 (Green bodies) | 1.72 | 0.26 | 1.02 |
| 2 (red/pass) | 1.25 | 0.26 | 1.02 |
| 3 (red/pass) | 1.3 | 0.23 | 1.07 |

**) It is not possible to carry out reduction reactions because the pellets are too soft.

The advantages of the catalyst pellets according to the invention (catalysts 2 and 3) can clearly be seen since these allow the introduction of larger amounts of catalyst pellets in reactors having a relatively large volume (e.g. a volume of a number of m³) and thus make it possible to carry out hydrogenations on an industrial scale, which is not possible when using the catalyst 1. Furthermore, the reactors can be filled significantly more densely with the catalyst pellets according to the invention (catalysts 2 and 3).

The invention claimed is:
1. A process for producing a shaped catalyst body, comprising
  a) providing a metal carbonate-comprising composition which comprises, based on the total weight of the metal carbonate-comprising composition,
    from 70 to 94.5% by weight of a metal carbonate mixture comprising two or more than two metal carbonates of two or more than two different metals (M),
    from 5 to 25% by weight of metallic copper, and
    from 0.5 to 5% by weight of tableting aid,
  b) forming a shaped body from the metal carbonate-comprising composition provided in step a), and
  c) activating the shaped body obtained in step b) in the presence of hydrogen at a temperature in the range from 150 to 250° C.

2. The process according to claim 1, wherein the shaped catalyst body obtained in step b) has a carbonate content in the range from 15 to 45% by weight before activation in step c).

3. The process according to claim 1, wherein the shaped body obtained in step b) is firstly subjected to a first thermal treatment at a temperature in the range from 150 to 350° C. in the absence of hydrogen in a step c1) and the shaped body which has been thermally treated in this way is subsequently activated at a temperature in the range from 150 to 250° C. in the presence of hydrogen in a step c2).

4. The process according to claim 3, wherein the shaped catalyst body obtained in step c1) has a carbonate content in the range from 0.1 to 2.5% by weight before activation in step c2).

5. The process according to claim 1, wherein the provision of the metal carbonate-comprising composition in step a) comprises the following steps
   a1) providing a pulverulent metal carbonate mixture comprising two or more than two metal carbonates of two or more than two different metals (M), and
   a2) adding the metallic copper and the tableting aid to the pulverulent metal carbonate mixture provided in step a1).

6. The process according to claim 1, wherein the shaped body is passivated at a temperature of 60° C. or less in the presence of an oxygen-comprising gas mixture after the activation in step c) or c2).

7. The process according to claim 1, wherein the metal carbonate mixture comprised in the metal carbonate-comprising composition comprises, based on the total weight of the metal carbonate mixture,
   from 40 to 65% by weight of copper carbonate,
   from 35 to 60% by weight of zinc carbonate, and
   from 0 to 20% by weight of a metal carbonate different from copper carbonate and zinc carbonate.

8. The process according to claim 1, wherein a molar ratio of copper carbonate and zinc carbonate in the metal carbonate mixture is in the range from 2:1 to 1:1.5.

9. The process according to claim 1, wherein the metal carbonate mixture comprised in the metal carbonate-comprising composition consists of
   from 40 to 65% by weight of copper carbonate, and
   from 35 to 60% by weight of zinc carbonate.

10. The process according to claim 1, wherein the metal carbonate mixture comprised in the metal carbonate-comprising composition comprises, based on the total weight of the metal carbonate mixture,
    from 22 to 36% by weight of copper, and
    from 18 to 33% by weight of zinc.

11. The process according to claim 1, comprising
    a) providing a metal carbonate-comprising composition which comprises, based on the total weight of the metal carbonate-comprising composition,
       from 70 to 94.5% by weight of a metal carbonate mixture comprising two or more than two metal carbonates of two or more than two different metals (M),
       from 5 to 25% by weight of metallic copper, and
       from 0.5 to 5% by weight of tableting aid,
    b) forming a shaped body from the metal carbonate-comprising composition provided in step a), and
    c) activating the shaped body obtained in step b) in the presence of hydrogen at a temperature in the range from 150 to 250° C.
    wherein the metal carbonate mixture comprised in the metal carbonate-comprising composition comprises, based on the total weight of the metal carbonate mixture,
    from 22 to 36% by weight of copper, and
    from 18 to 33% by weight of zinc.

12. The process according to claim 1, wherein the metal carbonate mixture comprises copper and zinc and a molar ratio of copper to zinc in the metal carbonate mixture is in the range from 2:1 to 1:1.5.

13. The process according to claim 10, wherein the molar ratio of copper to zinc is in the range from 2:1 to 1:1.5.

14. The process according to claim 1, wherein
    a) providing a metal carbonate-comprising composition which comprises, based on the total weight of the metal carbonate-comprising composition,
       from 70 to 94.5% by weight of a metal carbonate mixture comprising two or more than two metal carbonates of two or more than two different metals (M),
       from 5 to 25% by weight of metallic copper, and
       from 0.5 to 5% by weight of tableting aid,
    b) forming a shaped body from the metal carbonate-comprising composition provided in step a) and
    c) activating the shaped body obtained in step b) in the presence of hydrogen at a temperature in the range from 150 to 250° C.,
    wherein the metal carbonate mixture comprises copper and zinc and a molar ratio of copper to zinc in the metal carbonate mixture is in the range from 2:1 to 1:1.5.

15. The process according to claim 1, wherein the metallic copper is copper powder or copper flakes.

16. The process according to claim 1, wherein the tableting aid is selected from the group consisting of graphite, boron nitride, molybdenumdisulfide, and mixtures thereof.

17. A process for the hydrogenation of an organic compound having one or more than one carbonyl group(s), wherein the organic compound is brought into contact in the presence of hydrogen with a shaped catalyst body obtained by a process as claimed in claim 1.

18. The process according to claim 17, wherein the organic compound having one or more than one carbonyl group(s) comprises an ester compound.

19. The process according to claim 6 wherein the oxygen-comprising gas mixture is air.

20. The process according to claim 17 wherein the ester compound is a fatty acid ester.

* * * * *